(12) United States Patent
Hanft

(10) Patent No.: US 12,303,422 B2
(45) Date of Patent: May 20, 2025

(54) FOREFOOT ORTHOTIC DEVICE

(71) Applicant: FOREFOOT DEFENDER, LLC, Miami, FL (US)

(72) Inventor: Jason R. Hanft, Miami, FL (US)

(73) Assignee: Forefoot Defender, LLC, Miami, FL (US)

( * ) Notice: Subject to any disclaimer, the term of this patent is extended or adjusted under 35 U.S.C. 154(b) by 61 days.

(21) Appl. No.: 18/347,353

(22) Filed: Jul. 5, 2023

(65) Prior Publication Data

US 2023/0346584 A1    Nov. 2, 2023

Related U.S. Application Data

(63) Continuation of application No. 17/078,261, filed on Oct. 23, 2020, now abandoned, and a continuation of application No. 15/406,168, filed on Jan. 13, 2017, now abandoned.

(51) Int. Cl.
| | |
|---|---|
| *A61F 5/00* | (2006.01) |
| *A43B 7/1405* | (2022.01) |
| *A43B 7/144* | (2022.01) |
| *A43B 7/1445* | (2022.01) |
| *A43B 7/149* | (2022.01) |
| *A43B 17/00* | (2006.01) |
| *A43B 17/02* | (2006.01) |
| *A61F 5/01* | (2006.01) |
| *A61F 5/14* | (2022.01) |
| *A61F 13/04* | (2006.01) |

(52) U.S. Cl.
CPC ............... *A61F 5/14* (2013.01); *A43B 7/141* (2013.01); *A43B 7/144* (2013.01); *A43B 7/1445* (2013.01); *A43B 7/149* (2013.01); *A43B 17/006* (2013.01); *A43B 17/02* (2013.01); *A61F 5/0111* (2013.01); *A61F 13/045* (2013.01)

(58) Field of Classification Search
CPC ...... A61F 5/0111; A61F 5/019; A61F 5/0195; A61F 5/14; A61F 5/30; A61F 5/0127; A43B 17/00–18; A43B 13/186; A43B 19/00
USPC ............................................ 602/28, 29, 30
See application file for complete search history.

(56) References Cited

U.S. PATENT DOCUMENTS 2,089,384 A * 8/1937 Levitt ...................... A43B 7/22
36/145

* cited by examiner

*Primary Examiner* — Adam Baker
(74) *Attorney, Agent, or Firm* — RPG Law Group; Richard P. Gilly, Esq

(57) ABSTRACT

A forefoot orthotic device has multiple regions configured so that impact, propulsive or standing forces experienced by the forefoot of the user are accelerated, decelerated, shifted, transferred, or lessened, so as to promote pain reduction or otherwise address or treat conditions of the forefoot. In one implementation, the device includes expanded areas adapted to underlie the first and fifth metatarsal heads and cushion or offload forces therefrom. In still other variations, the device includes a plateau and regions adjacent the plateau and sloping downwardly therefrom, so that the time during which painful regions of the forefoot experience force, such as during gait or standing, is lessened in favor of transferring such forces to adjacent regions which potentially are less in need of treatment or protection from such forces.

20 Claims, 5 Drawing Sheets

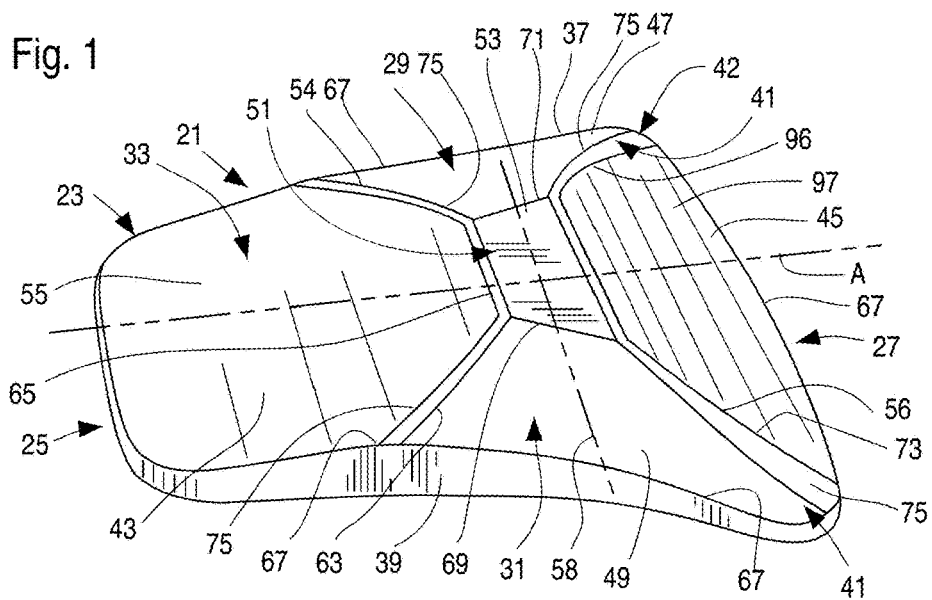
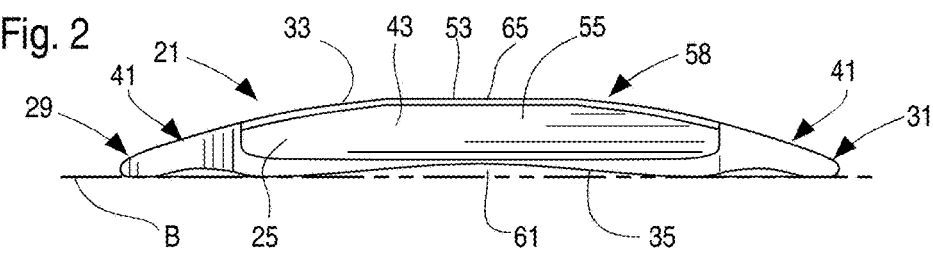
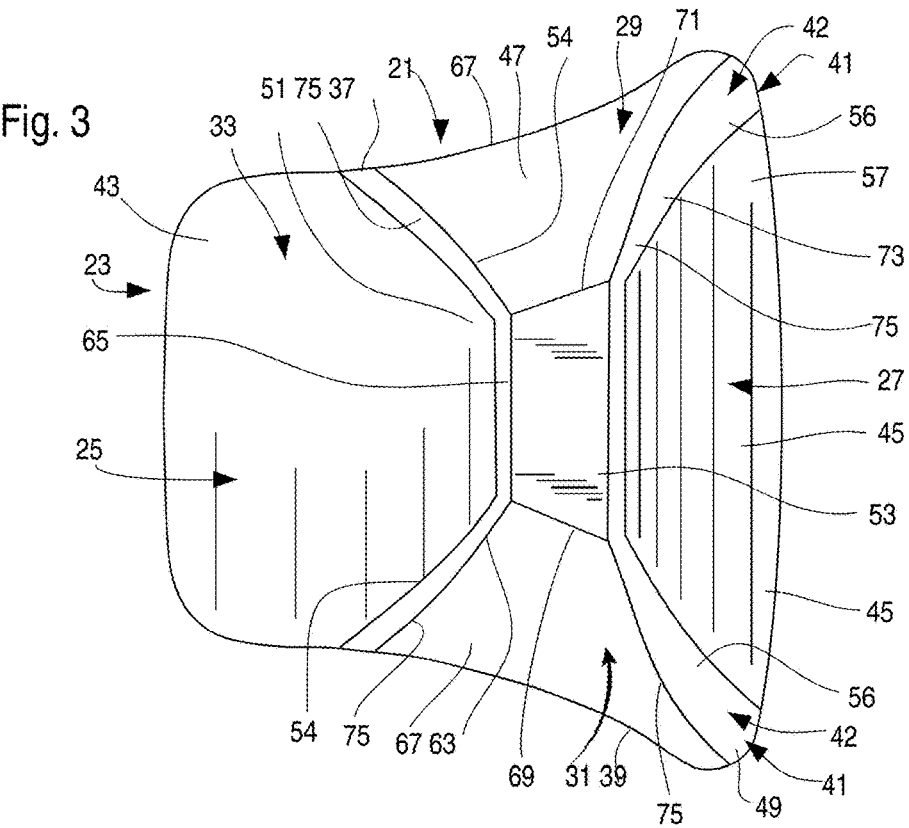

FOREFOOT ORTHOTIC DEVICE

FIELD

This disclosure relates to orthotic devices and, more particularly, to a forefoot orthotic device for use in connection with a user's foot.

BACKGROUND

Orthotic devices are useful for treating disorders, injuries, diseases or other harmful or painful foot conditions. Orthotic devices include metatarsal pads, often made of foam, and which cushion the metatarsal region of a user's foot which may overlie such pad, such as when such pad is inserted within footwear.

Orthotic devices for the forefoot of the current art suffer from various drawbacks and disadvantages.

Accordingly, there is a need for an improved forefoot orthotic device to address foot conditions of a user, including injuries, disorders, diseases and their associated trauma, pain, or other discomforts.

SUMMARY

In one possible implementation, a forefoot orthotic device for use in connection with the user's foot includes a resiliently compressible element sized and shaped to underlie the forefoot. The element is sized and shaped so that there are two, expanded areas of resiliently compressible material located toward the distal end of the element at respective lateral and medial sides. The expanded areas are transversely spaced from each other by a predetermined amount corresponding to the distance between the first and fifth metatarsal heads of the user's foot.

In further implementations, the forefoot orthotic device has an upper surface which extends upwardly and inwardly from the circumferential edge of the forefoot orthotic device, the surface having an upper portion defining a plateau raised relative to a lower plane of reference associated with the forefoot orthotic device.

In other variations of the disclosure, the resiliently compressible element includes lateral and medial areas which extend upwardly in a transverse direction so as to form an arch. The arch is located to underlie the metatarsal arch of the user's foot.

In still further versions of forefoot orthotic devices disclosed herein, the upper surface of the orthotic device has medial and lateral areas which are more rigid than portions of a proximal area adjacent to such medial and lateral areas. In this way, during use, deceleration of foot portions overlying the medial and lateral areas is greater than deceleration of foot portions overlying the adjacent portions of the proximal area, with the effect that force experienced in the metatarsal area is reduced or slowed in comparison to force experienced proximally thereto.

In still other variations, the medial and lateral areas of the upper surface are more rigid than portions of a distal area adjacent to such medial and lateral areas. As such, acceleration of forefoot portions overlying the distal area is greater than acceleration of forefoot portions overlying the medial and lateral areas.

In still further variations, devices according to the present disclosure may have a concavity formed in the lower surface of the resiliently compressible element, and the resiliently compressible material in such configuration is chosen so that weight or force associated with the user deflects the concavity toward a lower plane of reference during the gait cycle of such user, or in response to standing under load associated with the user's weight.

The forefoot orthotic device of the present disclosure includes features which take into account biomechanics of the user, both at various phases of the user's stance or gait, including the impact, swing, and propulsive phases of the user's gait, as well as points intermediate to such phases. The device is useful to address abnormalities or unique characteristics of a person's gait from whatever cause, whether from foot conditions or musculoskeletal factors.

BRIEF DESCRIPTION OF THE DRAWINGS

The disclosure herein will be more readily understood with reference to the drawings, in which:

FIG. 1 is an isometric view showing a forefoot orthotic device according to the present disclosure;

FIG. 2 is a rear-elevational view of the orthotic device of FIG. 1;

FIG. 3 is a top-plan view of the orthotic device of FIGS. 1-2;

DETAILED DESCRIPTION

Figure 4:
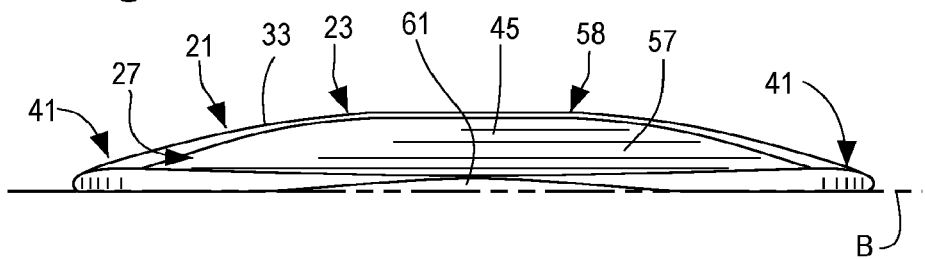
FIG. 4 is a front view of the orthotic device of FIGS. 1-3.
Figure 5:
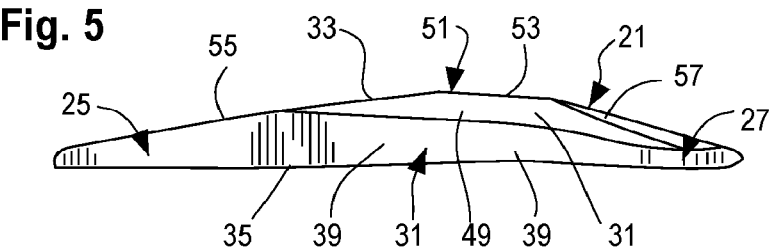
FIG. 5 is a side-elevational view of the orthotic device of FIGS. 1-4.
Figure 6:
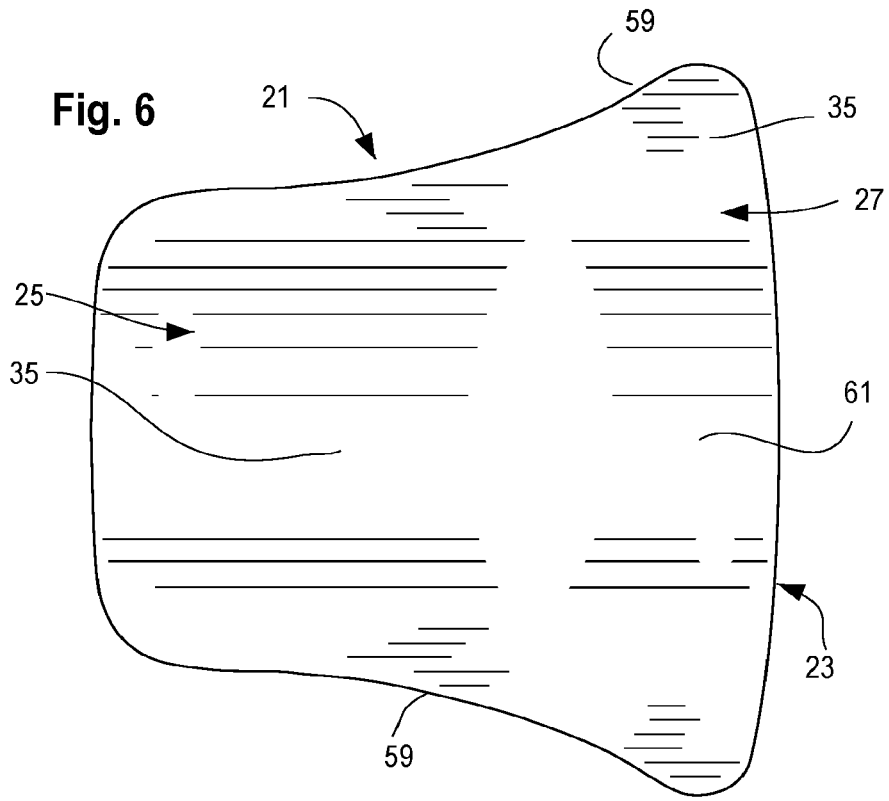
FIG. 6 is a bottom-plan view of the orthotic device of FIGS. 1-5.

Referring to the drawings, FIGS. 1-6 show a forefoot orthotic device 21, configured in this implementation to be an insert for use in footwear in connection with a user's foot. Orthotic device 21 comprises an element 23 formed of resiliently compressible material. Element 23 of the forefoot orthotic device 21 is shaped to have opposite proximal and distal ends 25, 27, opposite lateral and medial sides 29, 31, and opposite upper and lower surfaces 33, 35. The resiliently compressible material in this implementation extends between the opposite surfaces 33, 35, the opposite ends 25, 27, and the opposite sides 29, 31.

As further detailed in this disclosure, forefoot orthotic device 21 is constructed, shaped, sized or otherwise configured to address injury, disorder, pain, or other conditions of the forefoot, whether the user is standing or moving through the gait cycle. The features of device 21 reduce, alter, shift or offload force and pressures experienced by the forefoot at different times by the user while standing or during the gait cycle, so as to reduce forces otherwise experienced by anatomical features of the forefoot which cause pain or inhibit healing or other treatment of associated foot disorders.

To that end, element 23 is sized and shaped to underlie the forefoot of a user, with proximal end 25 positioned at the near or proximal end of the user's forefoot and distal end 27 positioned forward of proximal end 25, toward the forward or distal end of the user's forefoot.

Lateral and medial sides 29, 31 have respective side edges 37, 39. Side edges 29, 31 are located further from a central longitudinal axis A at distal end 27 than at proximal end 25. As such, element 23 has defined therein two, expanded areas 41 located at respective lateral and medial sides 29, 31, but expanded areas 41 are positioned toward distal end 27 of element 23, rather than at proximal end 25 thereof. In this way, expanded areas 41 are able to be positioned relative to the user's foot so as to underlie the first and fifth metatarsal heads of the user's foot. It will be appreciated by those skilled in the art that the lateral spacing of expanded areas 41 may range by certain predetermined amounts to correspond to the range of sizes of a potential user's foot, whether from child size 1 to adult male size 16. In this implementation, it has been found that predetermined spacing of expanded areas 41 may range between 2.5 inches to 3.5 inches, by predetermined amounts to correspond to corresponding foot sizes of the intended user.

Expanded areas 41 rapidly transition the first through fifth metatarsal head areas through the toe of phase of gait where there is high pressure and high forces on metatarsal heads into the propulsion and swing phase of the gait where there are lower pressures with minimal forces on the metatarsals.

Upper surface 33 includes certain features to reduce, alter, transfer, offload or otherwise relieve force experienced by the user's forefoot during standing (stance) or at various points during the user's gait cycle. For example, in this implementation, upper surface 33 extends upwardly and inwardly from opposite ends 25, 27 and opposite sides 29, 31, and thereby defines on upper surface 33 corresponding, opposite proximal and distal areas 43, 45 and opposite lateral and medial areas 47, 49. Areas 43, 45, 47, 49 have central portions 51 located inwardly from the edges of element 23 and, by virtue of the upward slope of upper surface 33, the central portions 51 together define a plateau 53 which is raised relative to a lower plane of reference B defined with reference to lower surface 35 of element 23. In other words, in this implementation, there are four areas 41, 43, 45, 47 which generally slope upwardly from the circumferential edge of element 23, the areas terminating in central portions which together define the plateau 53 at a raised elevation relative to the areas 43, 45, 47 and 49.

In one suitable implementation, lateral and medial areas 47,49 extend transversely from respective edges 37, 39 in an arch or arc to form a transverse arch 58 having a radius of curvature selected to provide support to the metatarsal arch of the user's foot. Arch 58 may have a radius of curvature of 80 mm to 110 mm for a size "large" orthotic for adult male sizes 8.5 to 15, and otherwise ranging −25% to +50% from that range for other implementations. In such implementation, the highest point of arch 58 is 8.2 mm relative to ground plane B, and may range −25% to +50% therefrom for other sizes or implementations. In other implementations. the top of arch 58 is located in plateau 53, and plateau 53 has a height ranging from 5 mm to 13 mm relative to ground plane B.

Lateral and medial areas 47, 49 may be formed of resiliently compressible material to make areas 47,49 firmer, more rigid, or otherwise less compressible than adjacent portions of proximal area 43. This physical characteristic may be achieved in a number of ways. For example, lateral and medial areas 47, 49 may have a higher durometer, may be formed of compressible material having different compressibility characteristics, or may employ different thicknesses or amounts of such compressible material, so that medial and lateral areas 47, 49 are more rigid than adjacent portions of proximal area 43. Since lateral and medial areas 47,49 are located closer to the user's metatarsal heads than proximal area 43, having lateral and medial areas more rigid than adjacent portions of proximal area 43, may have the effect that, during use, portions of the user's foot overlying lateral and medial areas 47, 49 are decelerated more than foot portions overlying the adjacent portions of proximal area 43. This may delay arrival of or lessen the force experienced by the metatarsal region of the forefoot overlying areas 47, 49 during the impact phase of the gait cycle. In other words, the spacial and angular relationship between proximal area 43 and lateral and medial areas 47, 49 of increased rigidity, slows the speed at which the metatarsal region of the user's forefoot distal to proximal area 43 receives force from the impact phase of the user's gait. Additionally, the presence of increased resiliency or rigidity in lateral and medial areas 47, 49 slows the rate at which the forefoot is fully loaded during standing or stance phase of the gait. In one suitable implementation, lateral and medial areas 47,49 have a thickness ranging from 2 mm to 20 mm whereas, distal and proximal areas 43, 45 adjacent thereto have thicknesses averaging 1 mm to 10 mm.

The slope and shape of lateral and medial areas 47, 49 direct force experienced by overlying forefoot portions laterally or medially, respectively. Additionally, areas 47, 49 accelerate transition from foot strike to propulsion for overlying forefoot portions during the gait cycle.

The greater rigidity, resilience, or stiffness of lateral and medial areas 47, 49 may be achieved by having resiliently compressible material of greater thickness at areas 47, 49 than in proximal area 43. Alternately or additionally, element 23 of orthotic device 21 may comprise resiliently compressible material having different physical or chemical characteristics at different regions of element 23, such that the compression load deflection value, rigidity, resilience or compressibility of the resiliently compressible material in lateral and medial areas 47, 49 is different from the characteristics of the resiliently compressible material in proximal area 43. Such differences can be tuned or selected so that, again, lateral and medial areas 47, 49 decelerate overlying foot portions more readily than foot portions overlying proximal area 43, again with the result of slowing down the arrival of impact force on the metatarsal area forward of proximal area 43 and allowing such forces to dwell in proximal area 43 for a greater period of time during the gait cycle, especially the impact phase thereof.

In another variation, distal area 45 may be shaped, configured or otherwise adapted to be less rigid, deflect more readily and/or have a compression load deflection value less than plateau 53 or lateral and medial areas 47, 49. In this way. under comparable load during use, acceleration of forefoot portions overlying distal area 45 is greater than acceleration of forefoot portions overlying lateral and medial areas 47, 49. As such, during stance or gait, weight or impact forces experienced in the metatarsal portions of the forefoot proximal or interior to distal area 45 are offloaded or directed toward distal area 45 so that sensitive or pain-prone regions of the forefoot overlying plateau 53 or lateral and medial areas 47, 49 are minimized, in favor of offloading toward less painful. stronger or otherwise more desirable regions toward the front of the user's forefoot or foot overlying distal area 45.

Distal area 45 may be shaped to slope toward the distal edge and toward lateral and medial edges to direct forces forward, as well as medially and laterally away from the midline of the foot.

Lateral and medial areas 47, 49 terminate in respective upper edges 54 which are located relatively higher than adjacent portions of proximal area 43 to define an uphill region 55, and likewise lateral and medial areas 47, 49 have distal edges 56 adjacent distal portion 45 located relatively higher than distal area 45 and thereby defining a downhill region 57 in distal area 45. As such, during the gait cycle, such as during impact phase, deceleration of foot portions overlying uphill region 55 is less than deceleration of foot portions overlying lateral and medial areas 47, 49, plateau 53, and arch 58 to delay impact force on metatarsal regions forward or distal to proximal area 43. At other points of the gait cycle, such as the end of the impact phase or in the beginning of the propulsive phase, downhill region 57 accelerates forefoot portions overlying distal area 45 more than forefoot portions overlying arch 58, medial areas 47, 49 or plateau 53, to encourage offloading or force transfer from anterior or proximal portions of the metatarsals or forefoot forward, such as toward upper metatarsal regions of the foot forward of the metatarsal heads. Force transfer or offload as described above likewise occurs when the user is standing or otherwise at stance phase.

In still other implementations of device 21, lower surface 35 has an outer circumference 59 and extends inwardly and upwardly therefrom relative to lower plane of reference B to form a concavity 61 between lower surface 35 and plane of reference B. The durometer, compression load deflection value, or other characteristics of the resiliently compressible material above concavity 61 may be selected so that force or weight associated with the user, whether standing or during the gait cycle, deflects or collapses concavity 61 toward lower plane of reference B, thereby reducing impact forces otherwise experienced by the forefoot such as on the metatarsal heads.

The characteristics of the resiliently compressible material defining concavity 61 may, likewise, be selected so that concavity 61 not only collapses toward lower plane of reference B, but may be selected so that the collapse occurs at points during the gait cycle when the foot portions overlying concavity 61 are impacting concavity 61, and the resiliency of concavity 61 is sufficient so that concavity 61 springs back when the force or weight exerted on concavity 61 by overlying portions of the foot are reduced. Otherwise stated, when foot portions overlying concavity 61 are impacting the ground or otherwise exerting sufficient force, concavity 61 will deflect and collapse toward lower plane of reference B, and when the impact phase of the gait cycle has completed and the user is in the toe-off or later phases of the gait cycle, concavity 61 will, at least partially return to its original shape in response to reduced force or weight being exerted by the overlying foot portion.

The particular sizes, shapes and physical characteristics of element 23 and its various components and areas may be varied to accomplish the force or weight transference described herein, the related acceleration or deceleration of overlying portions of the foot relative to each other, and to promote protection, healing or treatment of forefoot conditions of the user. In one suitable implementation, using the 00 durometer scale of ASTM Standard 2240, incorporated herein by reference, the resiliently compressible material of element 23 has values ranging from 20 to 80. Concavity 61 may be substantially dome shaped, having an average radius ranging from 12 mm to 25 mm. Concavity 61 may have a maximum depth ranging from 1 mm to 7 mm, with the point or area of maximum depth located below plateau 53. Plateau 53 may have a maximum height ranging from 5 mm to 13 mm. In one implementation, resiliently compressible material defining concavity 61 has a thickness of 4 mm, concavity 61 has a radius of 16-22 mm. and a maximum depth of 4 to 6 mm, with the resiliently compressible material having a durometer ranging from 40 to 50. Such configuration has been found suitable to cause concavity 61 to deflect or collapse during the impact phase of a user within the weight range of an average adult, and will, likewise, spring back during the toe-off or later phases of said user.

The thickness of resiliently compressible material between upper surface 33 and lower surface 35 may range from 4 mm to 12 mm. In certain implementations, thickness of resiliently compressible material between concavity 61 and plateau 53 may range between 4 mm and 6 mm. The foregoing thickness may be reduced toward the outer circumferential edges of element 23, especially the outer edges of proximal and distal ends 25, 27, to avoid overlying foot portions "feeling" discontinuities between element 23 and adjacent areas of the shoe, brace, boot, cast or insole.

In certain implementations, such as those illustrated, upper surface 33 of element 23 may be conceptually divided into the four areas discussed above, namely areas 43, 45, 47 and 49, as well as an additional plateau 53 defined at the inner portions of such areas. Plateau 53 may be considered a fifth area. In one variation, at least one of the areas, such as proximal area 43, extends upwardly from its proximal end 25 toward distal end 27 with an average angle of 9.2°, in one preferred implementation, but may also range from 8° to 10° in other implementations, and terminating in a first, U-shaped boundary 63. The U-shaped boundary 63 extends transversely from the lateral to the medial sides and has a corresponding first apex 65 located at a height of 8.2 mm in one implementation, or may also range from 5 mm to 12 mm relative to lower plane of reference B. The exact selection of height may vary −25% to +50% to correspond to a respective foot size of the user, such as sizes ranging from child size 1 to adult male size 16.

Lateral and medial sides 29, 31 and corresponding lateral and medial areas 47, 49 may be shaped and configured such that each of areas 47, 49 have a curvilinear, triangular shape with a base 67 located at the respective lateral or medial side 29, 31 and such triangular shape having tapering, curvilinear edges extending inwardly to second and third apices 69, 71. In the illustrated embodiment, first, second and third apices correspond to upper edges rather than single points, and define edges of plateau region 53, and second and third apices have a height ranging from 5 mm to 12 mm relative to lower plane B. The term apex or apices, as used herein, thus encompasses both high points as well as high edges.

Furthermore, distal area 45 may extend upwardly from the distal end toward plateau 53 with an average angle of 17.8° in one preferred implementation, or ranging from 15° to 20°, in other preferred implementations, terminating in a second, U-shaped boundary 73. The second, U-shaped boundary has a corresponding fourth apex which may either be a point or, as illustrated, an upper edge located at a height selected as 8.2 mm, or to range from 5 mm to 12 mm relative to lower plane B in other preferred implementations. The apex of distal area 45 may define a forward boundary of plateau 53.

As shown in FIGS. 1 and 3, expanded areas 41 include sloped portions 42 of lateral and medial areas 47, 49 and distal area 45, as well as portions of U-shaped boundary 73 and its associated bevel 75. In one implementation, U-shaped boundary 73 comprises the apex of sloped portions 42. Given that areas 41 are located to proximate to the likely position of metatarsal heads one and five of a user's foot when element 23 is in use. sloped portions 42 of expanded areas 41 act to transfer impact or propulsive forces otherwise experienced by metatarsal heads 1 and 5 medially in the case of metatarsal head 1 and laterally in the case of metatarsal head 5, thereby reducing forces likely to be experienced by metatarsal heads one and five. Sloped portions 42 may have multiple radii of curvature corresponding to the shapes of areas 45, 47, 49 and bevel 75. In one implementation, in expanded areas 41, areas 47, 49 have radii of curvature ranging from 90 mm to 100 mm. When features are described in terms of a radius of curvature, the center of curvature is located below upper surface 33, unless apparent otherwise by reference to the drawings or otherwise specified.

First and second U-shaped boundaries 63, 73 include bevels 75 characterized by having greater slope than respective adjacent portions of upper surface 33. Bevels 75 follow the contours of first and second boundaries 63, 73 in this variation, and have heights which decrease from the lateral, medial edge 37, 39 toward plateau 53, eventually becoming zero at plateau 53, so that bevels 75 terminate at plateau 53 and first and second boundaries 63, 73 are coplanar with plateau 53 at such upper termination point of bevels 75. Bevels 75 have radii of curvature (with center point of curvature located above upper surface 33) ranging from 2 mm to 5 mm.

Plateau 53 in the illustrated implementation is at the convergence of areas 43, 45, 47, and 49 of device 21. Its geometric shape and materials properties allow for support in the metatarsal arch area, thereby providing additional offloading of the metatarsal heads and forefoot.

Plateau 53 may be particularly effective during the time in which the heel is off the ground and the foot is transitioning between forefoot strike and propulsion. Plateau 53 provides upward pressure into the metatarsal arch, thereby increasing the reduction of ground forces and perceived pressure on the bottom of the foot.

Figure 7:
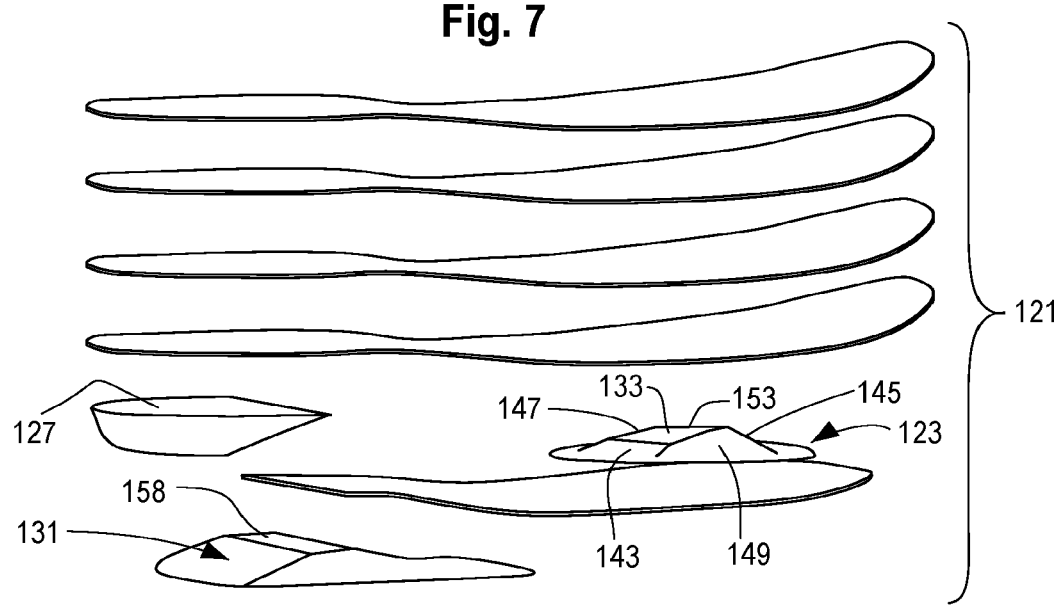
FIG. 7 is an exploded, isometric view of another implementation according to the present disclosure, in the form of an insole.
Figure 8:
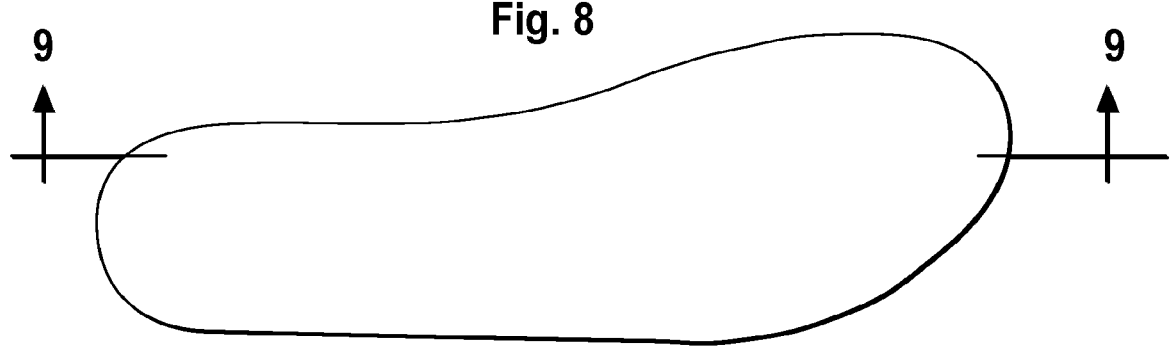
FIG. 8 is a top-plan view of the implementation of FIG. 7.
Figure 9:
FIG. 9 is a side-sectional view of the implementation of FIGS. 7-8.

Though the illustrated implementations of forefoot orthotic device 21 are suitable as inserts into footwear, the implementations of this disclosure include a forefoot orthotic device which comprises an insole 121, shown in FIGS. 7-9. Insole 121 is sized and shaped to underlie the foot of the user from the heel of the user and extending from the heel distally by an amount sufficient to underlie at least the metatarsal heads of the user's foot, such amount dictated by predetermined sizes of the user's foot ranging from child size 5 to adult male size 15, generally from 8" (20.3 cm) to 12½ (31.8 cm). In this implementation, insole 121 includes element 123 with upper surface 133 having expanded areas 141, a proximal area 243. a distal area 145, lateral and medial areas 47, 49 and a plateau 153, the foregoing areas having the features, shapes and configurations similar to those discussed with reference to element 23 in FIGS. 1-6. Element 123 is secured to insole 121 at a location adapted to underlie the forefoot of the user when insole 121 is in use. Element 123 may be integrated with the insole, either on the surface thereof, or within the insole as illustrated in FIG. 9. Insole 121 may be configured to allow removal of element 123 therefrom. In one implementation, insole for a size "large" as defined previously has a total length from heel to toe of 30 to 31 cm.

Optionally, insole 121 may be shaped to relieve pressure, provide support to, or otherwise treat areas of the foot other than the forefoot. For example, insole 121 may include a first portion 127 located on the "footprint" of the insole to underlie the user's heel and a second portion 131 distal to the first portion 127 and having an upper supporting surface 158 located to underlie the user's sagittal arch or mid-foot, distal to the calcaneal cuboid joint. Durometers (scale 00, ASTM 2240) for first portion 127 may be selected to range between 30 and 60, and second portion 131 to range between 45 and 70, with a relative difference preferably of between 10 and 20. Related teachings and disclosures of co-pending U.S. patent application Ser. No. 13/965,672, published as US 2015/0047221. entitled "Orthotic Insert Device," by the same inventor, are hereby incorporated by reference into this application.

The advantageous features of element 23, 123 may be adapted for use in any number of footwear environments, including shoes (including sneakers), boots, braces and casts, whether for protection, relief, treatment, or prophylactic use, and whether for temporary or continuous everyday use. Such footwear may incorporate element 23, 123 to treat forefoot conditions while the footwear is being worn. One implementation of the foregoing is shown in FIG. 10, wherein a brace 221 includes an insole having forefoot element 223 integrated therein.

Figure 10:
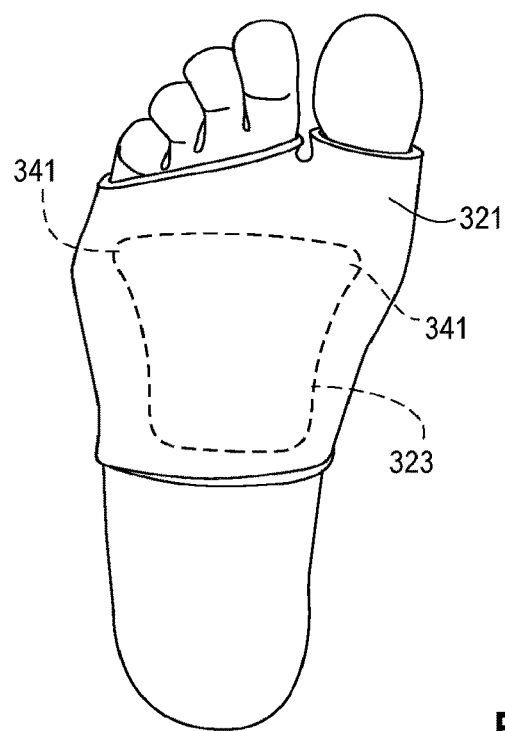
FIGS. 10 and 11 are bottom plan and isometric views, respectively, of another implementation according to the present disclosure in the form of a sleeve or sock.
Figure 11:
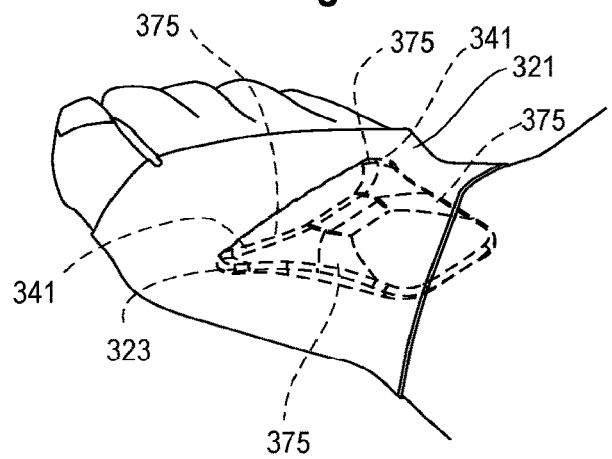
Figure 12:
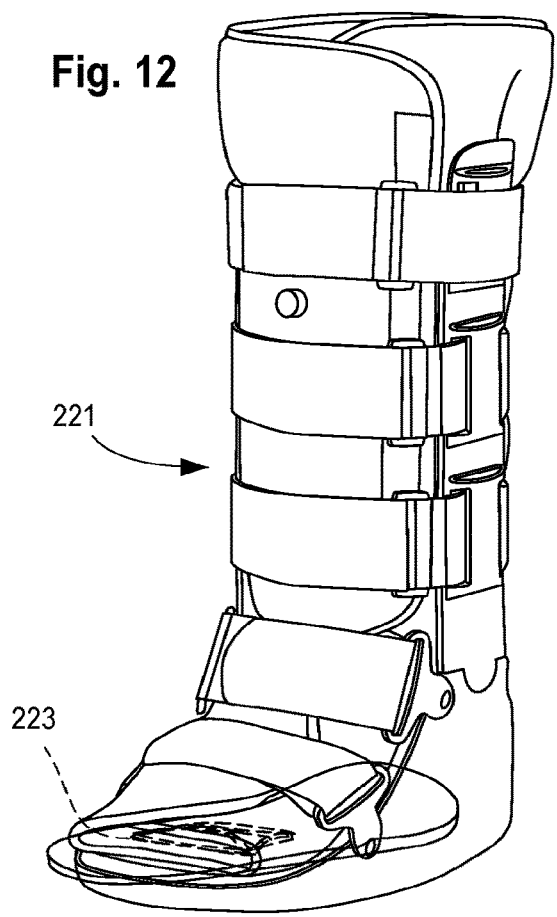
FIG. 12 is an isometric view of footwear according to the present disclosure.

Referring now to FIGS. 10 and 11, another implementation of this disclosure involves combining forefoot element 323 with a suitable sock or sleeve 321, which sleeve 321 is shown appropriately worn about the forefoot of a user in FIG. 10, so that expanded areas 341 are adjacent to or underlie metatarsal heads one and five, thereby obtaining the various functional advantages described with reference to the expanded areas of previous embodiments. Element 323 is substantially similar to elements 23, 123, 223 described previously and the combination of element 323 with a sock or sleeve 321 as shown permits the various treatment, pain relieving, and other therapeutic benefits described. In the implementation shown in FIGS. 10 and 11, bevels 375 are generally wider than corresponding bevels 75, have larger radii of curvature, ranging from 5 mm to 15 mm, and have widths ranging from 6 mm to 50 mm for proximal ones of bevels 375 and from 2 mm to 15 mm for the distal ones of bevels 375.

Having described the structures and features of forefoot orthotic devices 21, 121 and 221, their uses and advantages are apparent. The forefoot orthotic devices are inserted or fitted to one or both feet of a user to treat ailments, pain, disorders, amputations, or any number of other foot conditions affecting the forefoot and which may benefit from transfer or movement of forces arising during movement or weight at stance, from the regions of forefoot insult to adjacent regions where less pain may be experienced. Dimensions may be varied within a range corresponding to the respective foot size of the anticipated user.

Expanded areas 41, 141 are located to offload weight or force experienced by metatarsal heads one and five away from their normal point of contact with the ground, either by urging force forward of boundary 73 or laterally in the case of metatarsal head five, or medially in the case of metatarsal head one.

Testing has confirmed the various functions and advantageous features described herein in relation to the current art. As previously explained, the features described herein have been shown to decelerate the speed at which certain regions of the forefoot hit the ground in comparison to other forefoot regions at certain times of the gait cycle, and accelerate such speed at other times of the gait cycle. Pressure is decreased under the first through fifth metatarsals, especially by virtue of expanded areas 41 and arch 58 and underlying the metatarsal region. Standing or at stance, weight otherwise experienced in the metatarsal region is transferred from such region to adjacent regions which may be prone to less pain, or such transference may encourage healing of conditions by reducing weight-bearing activities. The combination of features described above decreases impact force in the forefoot region generally, decreases total time on portions of the forefoot, especially the metatarsal heads, and/or acts to decrease load on the forefoot relative to other portions of the foot.

Testing of certain implementations has shown that the features described herein decrease the area of the forefoot contacting the ground or shoe sole in favor of areas outside the forefoot experiencing such contact, and, thereby, force or pressure on the metatarsal heads is correspondingly reduced. These results are applicable whether at stance or during gait. During gait cycle, not only does the device decrease the pressure under all five metatarsal heads, according to tests results, but the length of time potentially sensitive areas of the forefoot are in contact with the ground is shortened as well, especially under the first and fifth metatarsal heads. resting has shown a 25-80% reduction in pressure or force on metatarsal heads and the forefoot region in general, and a 30-90% decrease in time that the metatarsal heads are experiencing forces otherwise associated with the gait cycle, such reductions being compared to the user's gait without the device described herein.

Figure 13A:
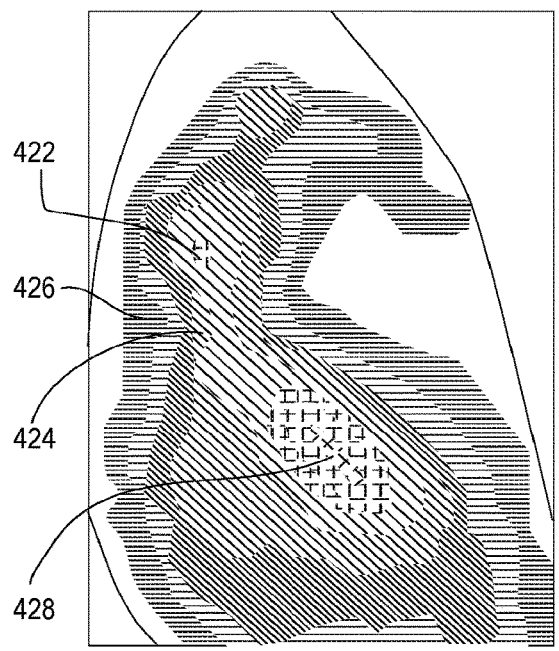
FIGS. 13 A&B and 14 A&B are orthotic scans showing pressure or force on the forefoot without and with an orthotic device according to the present disclosure.
Figure 13B:
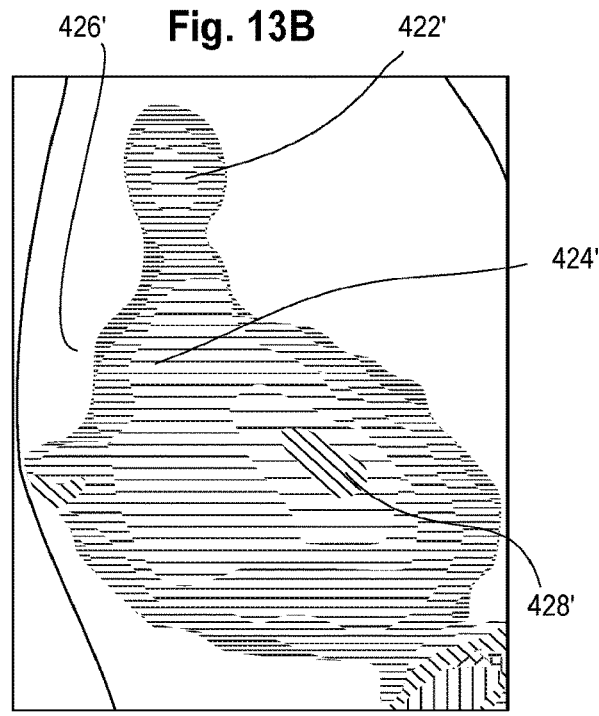

FIGS. 13A, 133, and 14A and 14B. are scans showing pressure or force on the forefoot without and with an orthotic device according to the present disclosure. FIGS. 13A, 13B show the forefoot of a left foot when standing, that is, statically, 13A corresponding to the forefoot without a device according to the present disclosure, and FIG. 13B showing pressure or force on the forefoot when a forefoot orthotic device according to the present disclosure is worn inside a shoe or other footwear. Referring to FIG. 13A, the scan of this test shows regions 422 corresponding to the great toe, and having green and yellow force bands which correspond to greater force or pressure on that region than on region 422 of FIG. 13B (ranging from blue to black) corresponding to the great toe overlying an orthotic device according to the present disclosure. Similarly, another region of greater pressure 424 shown in green in FIG. 13A corresponds to the first metatarsal head, and can be contrasted with a corresponding region of lower, pressure or force 424' (shown in blue) of FIG. 13B. Further, there is a substantial absence of pressure or force along portions of the first metatarsal shown at 425' (FIG. 13B) by a white region, in contrast to a blue region of greater force (426) shown in FIG. 13A. Still further, referring to FIG. 13A, force or pressure on metatarsal heads 2-5 is shown by color topography regions 428, including green, yellow and brown regions in FIG. 13A without an orthotic device, as opposed to the lesser forces or pressures on metatarsal heads 2-5 shown by the blue areas 428' in FIG. 13B.

Figure 14A:
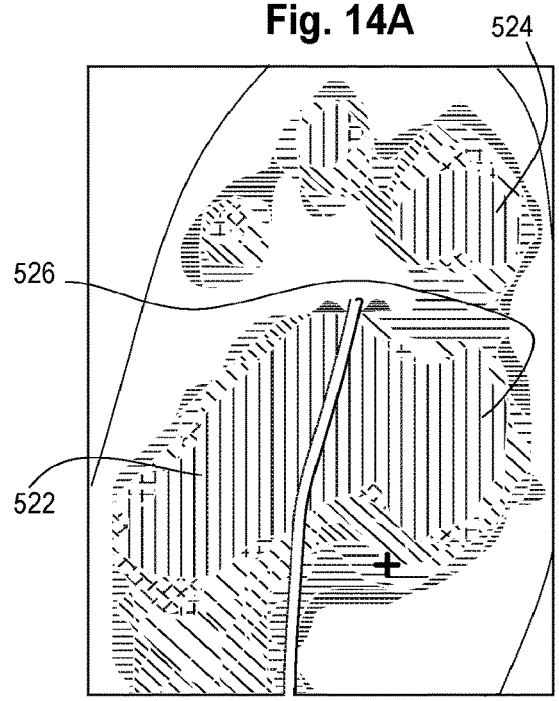
Figure 14B:
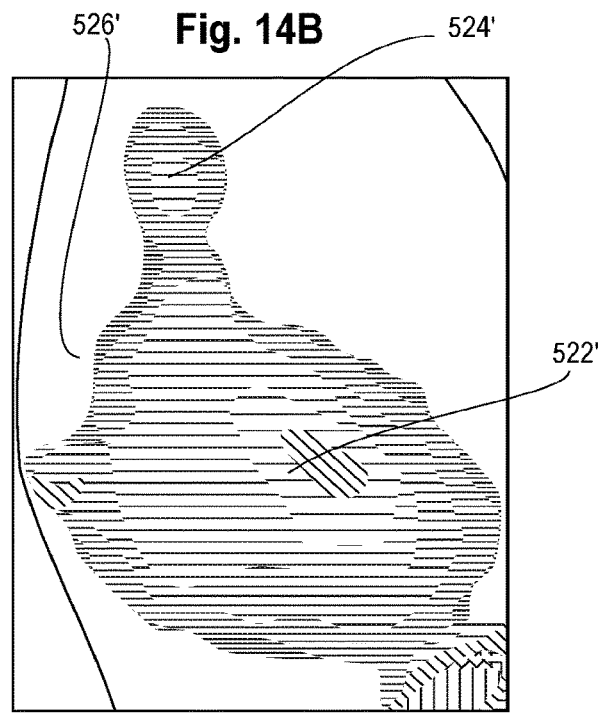

FIGS. 14A and 14B show dynamic test results of the forces or pressures on the forefoot without and with an orthotic device according to the present invention shown in terms of force or pressure experienced by the forefoot proximate to the moment of toe-off during the gait cycle. FIG. 14A is a left foot of a user without the device disclosed herein, and FIG. 14B is the right foot of the same user with an orthotic device as disclosed herein. Force or pressure in the regions of metatarsal heads one through five are shown with increased force or pressure without an orthotic device in region 522' of FIG. 14A with corresponding orange coloration, whereas metatarsal heads one through five have decreased force and pressure exerted thereon when overlying the disclosed orthotic device, as shown in FIG. 14B, at regions 522'. Furthermore, the first metatarsal, that is, the "great toe," experiences greater force shown as orange at region 524, without the orthotic device of the present disclosure, as opposed to the lower forces or pressure shown as blue or black in regions 522' in FIG. 14B corresponding to the great toe. As in the static test, the first metatarsal has an area of substantially reduced force or pressure (shown as white 526') in contrast to higher pressure in region 526 of the first metatarsal. shown by reference 526 in FIG. 14A. In general terms. the test results indicated in FIGS. 13A, 13B, and 14A, 14B, demonstrate how orthotic devices 21, 121, 221, 321, decrease contact area, that is, the area experiencing force, in the forefoot, and decrease pressure (that is, force) on metatarsal heads 1-5, including substantial decreases in reference to metatarsal one itself.

While one or more particular implementations have been set out in this disclosure, it will be appreciated that various alternatives to the disclosed structures are likewise contemplated and within the scope of this disclosure. For example, although element 23 has been illustrated as substantially comprising resiliently compressible material, other materials may be employed, such as non-compressible, flexible material, or non-resilient material. Suitable materials include foam, polymeric, metallic, thermoset or other suitable materials such as foam, plastic, metal, wood, cellulose or other non-foam or non-plastic materials, alone or in combination. Forefoot orthotic devices herein may employ cloth, antimicrobial, or other materials to enhance ease-of-use, longevity, or versatility. Element 23, 123, 223 may comprise a single molded piece, may consist of multiple substrates, or may be formed of multiple components fused together at opposing edges.

While the illustrated devices are substantially symmetric along longitudinal axis A (FIG. 1), other implementations may be asymmetric, may include only one of the expanded areas 41, or may be altered symmetrically or asymmetrically to account for left and right feet, or to account for other foot conditions.

Still further variations are contemplated by the disclosure herein, which should be understood to extend to the boundaries of the appended claims and equivalents thereto.

What is claimed is:

1. A forefoot orthotic device for use in connection with a user's foot, the user's foot characterized by a forefoot and metatarsal heads one through five, the device comprising:
   an element sized and shaped to underlie the forefoot, the element having opposite upper and lower surfaces, opposite proximal and distal ends, opposite lateral and medial sides, and resiliently compressible material extending between the opposite surfaces, the opposite ends and the opposite sides;
   wherein the element has a central longitudinal axis, the lower surface of the element having at least three points defining a lower plane of reference for the element when the device is in use;
   wherein the lateral and medial sides have respective lateral and medial side edges, the lateral and medial side edges located further from the central longitudinal axis at the distal end than at the proximal end;
   a first and a second, substantially symmetrical expanded areas located at the lateral and medial sides, respectively, on the distal end of the element;
   wherein the expanded areas are laterally spaced from each other by a predetermined amount and face upwardly to underlie the first and the fifth metatarsal heads of the user's foot when received on the device, the predetermined amount corresponding to a distance between the first and fifth metatarsal heads of the user's foot selected as a function of an intended size of the user's foot, the intended size ranging from child size 1 to adult male size 16 and corresponding to between 2.5 inches and 3.5 inches;

wherein the upper surface extends upwardly and inwardly from the opposite ends and the opposite sides to define corresponding, opposite proximal and distal areas, and opposite lateral and medial areas, the proximal, distal, medial, and lateral areas having respective central portions defining a plateau raised relative to the lower plane of reference; and wherein the resiliently compressible material of the element is configured so that the lateral and medial areas are more rigid than portions of the proximal area adjacent the medial and lateral areas to delay arrival of impact force on regions of the forefoot overlying the medial and lateral areas relative to regions of the forefoot overlying the adjacent portions of the proximal area during an impact phase of a gait of the user.

2. The device of claim 1, wherein the lateral and medial areas extend transversely in an arch from the lateral and medial side edges, the arch having a radius of curvature ranging from 80 mm to 110 mm.

3. The device of claim 2, wherein the arch comprises a top, and wherein the top of the arch is located in the plateau.

4. The device of claim 1, wherein the resiliently compressible material under the medial and lateral areas is thicker than the resiliently compressible material under the adjacent portions of the proximal area.

5. The device of claim 4, wherein the thicker resiliently compressible material of the medial and lateral areas terminates in an upper edge relatively higher than the adjacent portions of the proximal area to define an uphill region on the upper surface of the element.

6. The device of claim 1, wherein the lower surface has a circumference and extends inwardly and upwardly therefrom relative to the lower plane of reference to define a concavity, and wherein the resiliently compressible material is configured so that weight associated with the user deflects the concavity toward the lower plane of reference.

7. The device of claim 6, wherein the resiliently compressible material is configured to have a thickness ranging between 4 mm and 6 mm, a durometer, according to a 00 scale, ranging from 20 to 80, and wherein the concavity is defined to have a radius ranging from 16 mm to 22 mm and a maximum depth ranging from 4 mm to 6 mm, whereby the concavity returns from a deflected position during impact phase of the gait cycle to an un-deflected position after toe-off phase of a gait cycle of the user.

8. The device of claim 1, wherein the device includes an insole sized and shaped to underlie the foot of the user from the heel of the user, the insole extending from the heel distally by an amount ranging from 20 cm to 31.8 cm sufficient to underlie at least the metatarsal heads of the user's foot, and wherein the element is secured to the insole in a location to underlie the metatarsal heads of the user when the device is in use.

9. The device of claim 8, wherein the element is integrated with the insole.

10. The device of claim 9 in which the user's foot includes a heel, a mid-foot, and an associated sagittal arch, wherein the insole includes a first portion underlying the heel and having a first predetermined durometer and a second portion underlying the sagittal arch of the mid-foot and having a second predetermined durometer, and wherein the second predetermined durometer is greater than the first predetermined durometer by amounts ranging between 10 and 20.

11. The device of claim 1, wherein the device includes a sleeve sized and shaped to be worn about the forefoot of the user, wherein the element is secured to the sleeve in a location to underlie the forefoot of the user when the device is in use.

12. The device of claim 1, wherein the device includes footwear selected from the group consisting of a shoe, boot, brace and cast, the footwear having a sole positioned under the user's foot when received in the device, and wherein the element is disposed on the sole and positioned thereon to have the upper surface of the element underlying the forefoot of the user when the foot is placed in the device.

13. The device of claim 12, wherein the footwear portions include an insole disposed above the sole, and wherein the element is secured to or integrated with the insole.

14. A forefoot orthotic device for use in connection with a user's foot, the user's foot characterized by a forefoot and metatarsal heads one through five, the device comprising:

an element sized and shaped to underlie the forefoot, the element having opposite upper and lower surfaces, opposite proximal and distal ends, opposite lateral and medial sides, and resiliently compressible material extending between the opposite surfaces, the opposite ends and the opposite sides;

wherein the element has a central longitudinal axis, the lower surface of the element having at least three points defining a lower plane of reference for the element when the device is in use;

wherein the lateral and medial sides have respective lateral and medial side edges, the lateral and medial side edges located further from the central longitudinal axis at the distal end than at the proximal end;

at least two substantially symmetrical expanded areas located at the lateral and medial sides, respectively, on the distal end of the element:

wherein the expanded areas are laterally spaced from each other by a predetermined amount and face upwardly to underlie the first and the fifth metatarsal heads of the user's foot when received on the device, the predetermined amount corresponding to a distance between the first and fifth metatarsal heads of the user's foot selected as a function of an intended size of the user's foot, the intended size ranging from child size 1 to adult male size 16 and corresponding to between 2.5 inches and 3.5 inches;

wherein the upper surface extends upwardly and inwardly from the opposite ends and the opposite sides to define corresponding, opposite proximal and distal areas, and opposite lateral and medial areas, the proximal, distal, medial, and lateral areas having respective central portions defining a plateau raised relative to the lower plane of reference; and wherein the resiliently compressible material of the element is configured so that the medial and lateral areas are more rigid than portions of the distal area adjacent the medial and lateral areas to offload weight while the user is standing or impact forces during a toe-off phase of the user's gait from regions of the forefoot proximal of the distal area toward regions of the forefoot overlying the distal area.

15. A forefoot orthotic device for use in connection with a user's foot, the user's foot characterized by a forefoot and metatarsal heads one through five, the device comprising:

an element sized and shaped to underlie the forefoot, the element having opposite upper and lower surfaces, opposite proximal and distal ends, opposite lateral and medial sides, and resiliently compressible material extending between the opposite surfaces, the opposite ends and the opposite sides;

wherein the element has a central longitudinal axis, the lower surface of the element having at least three points defining a lower plane of reference for the element when the device is in use;

wherein the lateral and medial sides have respective lateral and medial side edges, the lateral and medial side edges located further from the central longitudinal axis at the distal end than at the proximal end;

two substantially symmetrical expanded areas located at the lateral and medial sides, respectively, on the distal end of the element;

wherein the expanded areas are laterally spaced from each other by a predetermined amount and face upwardly to underlie the first and the fifth metatarsal heads of the user's foot when received on the device, the predetermined amount corresponding to a distance between the first and fifth metatarsal heads of the user's foot selected as a function of an intended size of the user's foot, the intended size ranging from child size 1 to adult male size 16 and corresponding to between 2.5 inches and 3.5 inches;

wherein the upper surface extends upwardly and inwardly from the opposite ends and the opposite sides to define corresponding, opposite proximal and distal areas, and opposite lateral and medial areas, the proximal, distal, medial, and lateral areas having respective central portions defining a plateau raised relative to the lower plane of reference;

wherein the lower surface has a circumference and extends inwardly and upwardly therefrom relative to the lower plane of reference to define a concavity, and wherein the resiliently compressible material and the concavity are dimensioned to deflect the concavity toward the lower plane of reference prior to a toe-off phase while in use during a gait cycle of the user and to return the concavity from the deflected position to an un-deflected position after the toe-off phase of the gait cycle of the user.

16. The device of claim 15, wherein the resiliently compressible material is configured to have a thickness ranging between 4 mm and 6 mm, a durometer, according to a 00 scale, ranging from 20 to 80, and wherein the concavity is defined to have a radius ranging from 16 mm to 22 mm and a maximum depth ranging from 4 mm to 6 mm.

17. The device of claim 15, wherein the resiliently compressible material of the element is configured so that the lateral and medial areas are more rigid than portions of the proximal area adjacent the medial and lateral areas, whereby, during an impact phase while in use, deceleration of regions of the foot overlying the medial and lateral areas is greater than deceleration of regions of the foot overlying the adjacent portions of the proximal area, wherein the resiliently compressible material of the element is configured so that the medial and lateral areas are more rigid than portions of the distal area adjacent the medial and lateral areas, whereby, during the toe-off phase while in use, acceleration of forefoot portions overlying the distal area is greater than acceleration of forefoot portions overlying the medial and lateral areas.

18. The device of claim 17, wherein the resiliently compressible material under the medial and lateral areas is thicker than the resiliently compressible material under the adjacent portions of the proximal area.

19. The device of claim 18, wherein the thicker resiliently compressible material of the medial and lateral areas terminates in an upper edge relatively higher than the adjacent portions of the proximal area to define an uphill region on the upper surface of the element.

20. The device of claim 15, wherein the device includes footwear selected from the group consisting of a shoe, boot, brace and cast, the footwear having a sole positioned under the user's foot when received in the device, and wherein the element is disposed on the sole and positioned thereon to have the upper surface of the element underlying the forefoot of the user when the foot is placed in the device.

* * * * *